United States Patent [19]
Schmidt

[11] Patent Number: 5,707,374
[45] Date of Patent: Jan. 13, 1998

[54] APPARATUS FOR PREPARING THE MEDULLARY CAVITY

[75] Inventor: Joachim Schmidt, Gladbach, Germany

[73] Assignee: Merck Patent Gesellschaft mit Beschrankter Haftung, Darmstadt, Germany

[21] Appl. No.: 659,816

[22] Filed: Jun. 7, 1996

[30] Foreign Application Priority Data

Jun. 9, 1995 [DE] Germany .......................... 195 21 053.0

[51] Int. Cl.⁶ .................................................. A61B 17/16
[52] U.S. Cl. ................................................ 606/85; 606/80
[58] Field of Search .................... 606/84, 85, 89, 606/95, 99, 91, 92, 94

[56] References Cited

U.S. PATENT DOCUMENTS

D. 272,648  2/1984  Bolesky et al. .......................... 606/85

FOREIGN PATENT DOCUMENTS 296986  12/1988  European Pat. Off. ................. 606/85
3907256  9/1990  Germany ................................. 606/85

Primary Examiner—Michael Buiz
Assistant Examiner—Julian W. Woo
Attorney, Agent, or Firm—Millen, White, Zelano, & Branigan, P.C.

[57] ABSTRACT

The invention relates to equipment consisting of awl and rasp for preparing the medullary cavity when implanting endoprostheses in long bones. According to the invention, each of the shafts is designed as a hollow body. At the cutting teeth arranged on the outer side of the shaft, there are openings which are directed into the shaft interior. The excavated material collects in the hollow space of the awl or rasp shaft and can be removed from there via apertures at the proximal end and distal end of the shaft by irrigation and/or suction, or is removed together with the instrument after the latter has been used.

5 Claims, 3 Drawing Sheets

APPARATUS FOR PREPARING THE MEDULLARY CAVITY

FIELD OF THE INVENTION

The invention relates to equipment for preparing the medullary cavity when implanting endoprostheses in long bones. This equipment consists of an awl and a rasp.

BACKGROUND OF THE INVENTION

Whenever implanting prostheses in the medullary cavity of a long bone (femoral shaft proximal to the hip, humeral shaft proximal to the shoulder, tibial/femoral shaft proximal to the knee joint, etc.), this medullary cavity has to be prepared for the shape and size of the selected prosthesis. A point which has to be taken into consideration in this respect is whether the prosthesis is intended to be anchored with or without cement. This preparatory work is generally carried out using awls and rasps which are adapted to the subsequent prosthesis shape. For this purpose, after opening the bone, for example by removing the condyle, the spongy substance and marrow have to be excavated and a bearing created for receiving the prosthesis shaft. This space must be dimensioned so that the prosthesis wedges firmly without cement, or so that sufficient room is left for cemented anchoring and the cement interlocks with the remaining trabeculae of the spongy substance.

In the case of current awls and rasps of this type, which are generally made of a metallic material, the dimensioning and the external shape of their shafts correspond exactly or very substantially to the shaft of the prosthesis which is to be implanted. The awl normally has a cylindrical shaft, while the rasp imitates the actual prosthesis shaft. The outer surface of the awl shaft or rasp shaft is equipped with sharp teeth. By introducing the awl shaft into the medullary cavity, generally in a rotational movement in a clockwise direction, the medullary cavity is opened up and prepared axially true. By pressing the rasp shaft into the opened long bone and moving the shaft up and down or to and fro, a suitable bearing is created for the prosthesis.

In the case of the previous awls and rasps, the excavated material, mainly bone chips, remains in the medullary cavity. There, the excavated material is further ground down and mixes with blood, soft tissue, any irrigating liquid which may be present, etc. As a result of the movements of the rasp, this mixture of excavated material forces its way mainly through the opening in the bone near the joint and there disperses into the soft-tissue parts, unless it can be sufficiently collected and removed. Some of it forces its way into the honeycombs of the spongy substance, while some forces its way peripherally into the medullary cavity. In order to prevent the excavated material from pressing into the honeycombs of the spongy substance, or in order to re-open these honeycombs, the instrument has to be removed frequently during the preparation of the medullary cavity in order to irrigate the said medullary cavity. The irrigating liquid also disperses into the soft-tissue parts near the joint.

Such instruments and their method of handling have disadvantages:

The flood of bone substance into the soft-tissue parts is held responsible, inter alia, for the development of heterotopic ossification, which adversely are then removed with the respective instrument.

It is advantageous for the excavated material collecting in the shaft interior to be drawn off by suction. For this purpose, the proximal end of the instrument is expediently provided with an aperture which reaches into the interior and through which a suction device can be introduced or can be connected via a connection device.

The removal of the excavated material can additionally be promoted by periodic or continuous irrigation. For this purpose, it is expedient to connect a combined irrigating and suctioning device at the proximal aperture of the awl shaft or rasp shaft, through which device irrigating liquid is guided into and through the interior of the instrument, for instance by way of a cannula. It is particularly advantageous if the instrument also has an aperture at the distal end. If the end of the irrigation cannula reaches as far as this aperture, or reaches through the said aperture into the medullary cavity, then the irrigating liquid principally washes round the outside of the awl body or rasp body, and the excavated material is guided particularly effectively through the openings at the cutting teeth and into the interior of the shaft, from where the said excavated material can be drawn off by suction.

In the case of the embodiment of the instruments with additional apertures at the proximal end and distal end, these can also be guided via a centering device in a manner known per se for the corresponding prostheses. A rod can be used as this type of centering device, this affects the results in, for example, 30% to 80% of hip endoprostheses.

The honeycombs of the spongy substance are closed by the excavated material. Cement cannot penetrate into these honeycombs for anchoring purposes and thus cannot adequately interlock either.

During the work involved in introducing the cement, or when introducing the prosthesis, excavated material present in the honeycombs of the spongy substance can be forced into the blood flow and trigger a fat-embolism syndrome.

During the preparation of the medullary cavity, the equipment must therefore be removed frequently in order to flush the excavated material out of the medullary space.

SUMMARY OF THE INVENTION

The objection of the present invention is therefore to produce equipment which is used for preparing the medullary cavity for endoprosthetic surgery of long bones and which does not have the disadvantages which are described above.

According to the invention, this is achieved by means of equipment consisting of awl and rasp for preparing the medullary cavity, each of the shafts being designed as a hollow body, and their cutting teeth having openings which are directed into the shaft interior. By means of these structural measures, the awls and rasps according to the invention ensure that, when they are handled in the conventional manner, bone chips and bone-marrow constituents are guided into the shaft interior. They are collected there as the preparation of the medullary cavity proceeds, and they are then removed with the respective instrument.

It is advantageous for the excavated material collecting in the shaft interior to be drawn off by suction. For this purpose, the proximal end of the instrument is expediently provided with an aperture which reaches into the interior and through which a suction device can be introduced or can be connected via a connection device.

The removal of the excavated material can additionally be promoted by periodic or continuous irrigation. For this purpose, it is expedient to connect a combined irrigating and suctioning device at the proximal aperture of the awl shaft or rasp shaft, through which device irrigating liquid is guided into and through the interior of the instrument, for instance by way of a cannula. It is particularly advantageous if the instrument also has an aperture at the distal end. If the end of the irrigation cannula reaches as far as this aperture, or reaches through the said aperture into the medullary cavity, then the irrigating liquid principally washes round the outside of the awl body or rasp body, and the excavated material is guided particularly effectively through the openings at the cutting teeth and into the interior of the shaft, from where the said excavated material can be drawn off by suction.

In the case of the embodiment of the instruments with additional apertures at the proximal end and distal end, these can also be guided via a centering device in a manner known per se for the corresponding prostheses. A rod can be used as this type of centering device, this rod being arranged on a medullary cavity blocker which has been fitted beforehand in the medullary cavity. The centering device and irrigation cannular can also be present in combination.

The advantages which can be achieved with the invention are:

A flooding of bone-marrow constituents into the soft-tissue parts near the joint is avoided.

Excavated material is prevented from pressing into the honeycombs of the spongy substance.

The infiltration of the constituents of the medullary cavity into the blood flow (fat-embolism syndrome) is reduced since, on the one hand, no excavated material can be forced out of the honeycombs of the spongy substance into the blood flow, and, on the other hand, the open structure of the instrument prevents a pathological buildup of pressure.

A better strengthening of the trabeculae of the spongy substance is achieved upon cementing, since the honeycombs of the spongy substance are not closed off by excavated material.

The operating procedure is accelerated, since it is possible to dispense with the intermediate irrigation which was hitherto necessary.

In addition, in the case of the equipment according to the invention, the open structure, in contrast to the otherwise customary closed solid bodies, prevents an intramedullary increase in pressure, with initiation of a fat-embolism syndrome.

The equipment according to the invention for preparing the medullary cavity can be used in all types of implantation of prostheses in medullary cavities (Femur, humerus, tibia, etc.), and with cemented or cementless anchoring of the prostheses.

The awl or rasp is manufactured in the shape and size corresponding to the respective prosthesis and is used in the usual way. In the case of continuous suctioning, a suction device is additionally connected to the instrument. In the case of additional direct irrigation, an irrigating system is also connected. During the preparation of the medullary cavity, an additional flushing-out of the said medullary cavity can be dispensed with completely or can be reduced to a minimum. Spread of bone substance into the soft-tissue parts is thus to be avoided.

The invention is described in greater detail hereinbelow, with an awl and a rasp for a femoral prosthesis being used as an example.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
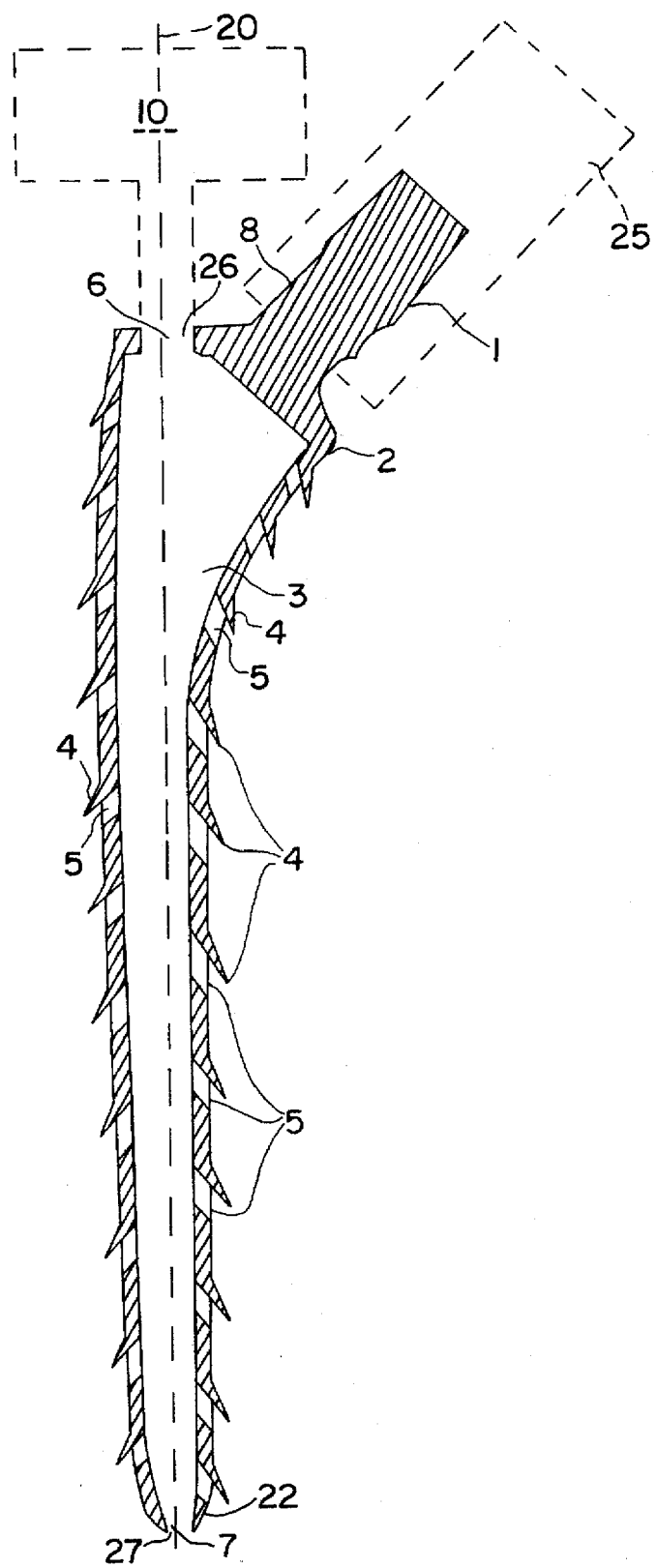
FIG. 1 is a side view, in elevation, of a rasp configured as a hollow shape in the shape of a prosthesis with a suction device schematically shown attached thereto.
Figure 2:
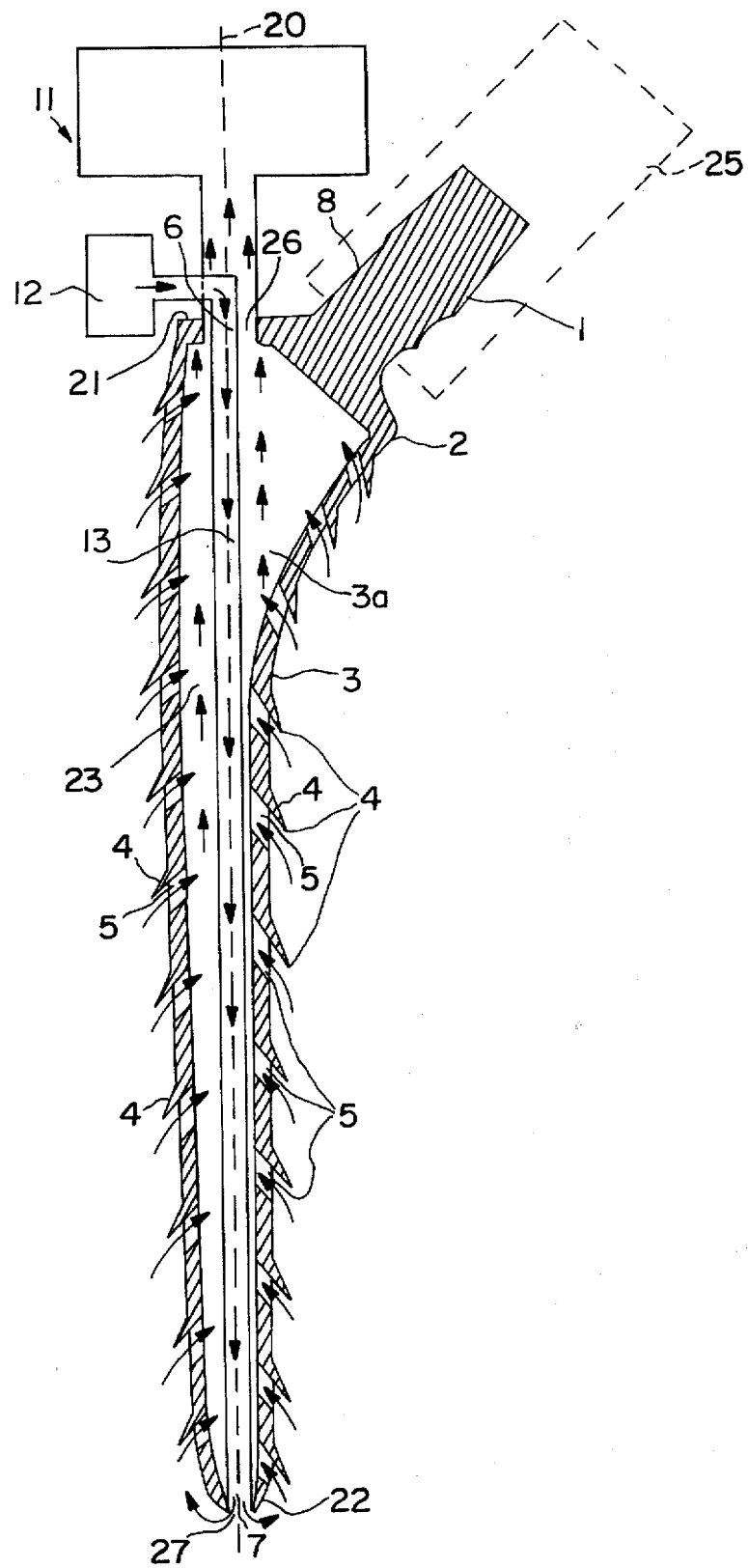
FIG. 2 is a view similar to FIG. 1 but including an irrigation device as well as a suction device.
Figure 3:
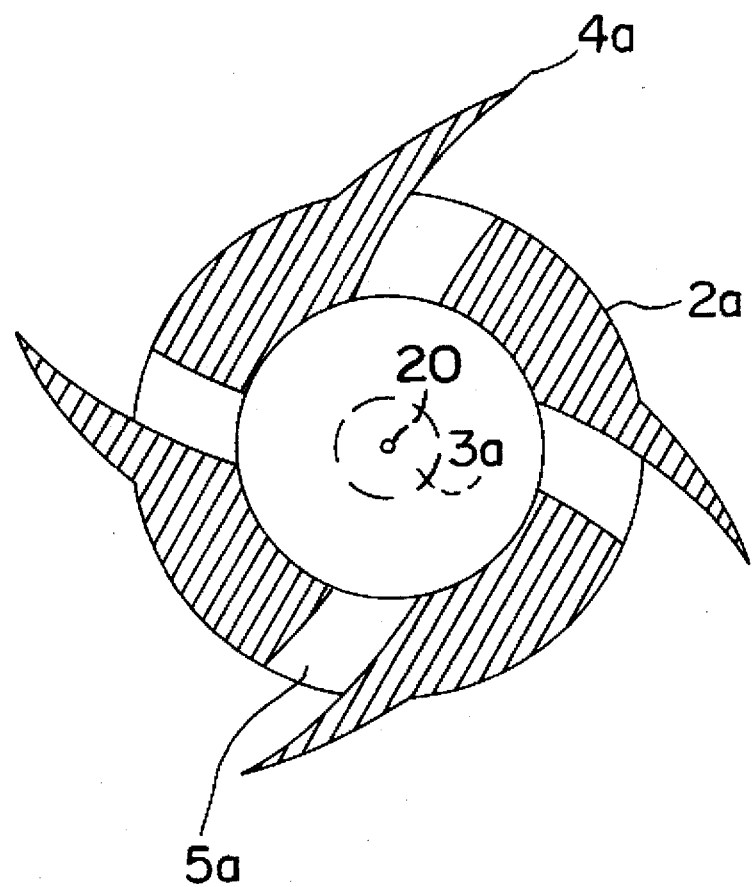
FIG. 3 is a cross-section of an awl, which awl has radially projecting teeth with axially extending edges.

FIGS. 1 and 2 show, by way of an illustrative embodiment, a rasp in longitudinal section. The rasp 1 corresponds in its external shape to conventional rasps for femoral prostheses. The rasp shaft in particular imitates the prosthesis shaft. After the condyle has been resected and the medullary cavity has been prepared, this instrument is used to create the bearing for the prosthesis shaft by being axially reciprocated in the cavity.

The rasp shaft 2 is designed as a hollow body 3 with a bore 3a. Cutting teeth 4 are arranged on the outside of the shaft, which cutting teeth 4 are directed obliquely downwards. At the inner flanks of the cutting teeth there are openings which, in accordance with the position of the cutting teeth, are directed into the interior of the rasp shaft designed as the hollow body 3. At the proximal and distal ends of the rasp shaft, there are apertures 6 and 7, respectively. A centering device (not shown) can be guided through these apertures, if approximate. In addition, a suction device 10 (FIG. 1) or a combined irrigation and suction device 11 (FIG. 2) can be connected at the proximal aperture 6. With the combined irrigation and suction device 11, liquid is introduced from a source 12, flows down a central tube 13 in the bore 3a and out of opening 7 in the distal end. The liquid returns through openings 5 to the bore 3a to a suction source 14. The neck area and cone area 8 of the rasp can be designed in a manner known per se and can be provided in particular for receiving the rasp or for receiving a specimen head.

FIG. 2 shows an awl in cross-section. After the condyle has been resected, the medullary cavity is prepared with this instrument by means of the latter being introduced into the bone cavity with rotational movement, here in a clockwise direction, and excavating the bone. Cutting teeth 4a, directed towards to the side rather than downwardly are located on the awl shaft 2a designed as a hollow body 3a. The openings 5a leading to the instrument interior 3a follow the direction of the teeth.

The edges 16 of the teeth 4 face toward the distal end (opening 7) of the rasp 1, while the edges 17 of the teeth 4a extend in the axial direction of the awl 1a.

In summary, apparatus 1 is disclosed in FIG. 2 for preparing a medullary cavity during endoprosthetic surgery of long bones, wherein the apparatus comprises a hollow shaft 2 formed about an axis 20 and having a first end 21 and a second end 22, wherein the hollow shaft defines a wall surrounding a central bore 23. There is an offset lug 8 on the first end 21 of the hollow shaft 2. The lug 1 extends obliquely with respect to the axis 20 and is adapted to receive a handle 25. Adjacent the lug 8 is a first opening 26 which communicates with the bore 23. A second opening 27 extends through the second end 22 of the hollow shaft 2. The first opening receives the central tube 13 extending from the source of fluid 12 for irrigation and also providing a connection to the suction device 11. Liquid flowing down the tube 13 enters the medullary cavity of the bone open exiting from the opening 27 to provide irrigating fluid and is aspirated from the cavity by the passages 5.

The spaced peripheral teeth 4 extend radially outwardly from the wall of the shaft 2 and have cutting edges 4a for removing material from the wall of the medullary cavity. Since the passages 5 are adjacent the peripheral teeth 4 and communicate with the bore 23 of the shaft, material removed by the teeth is entrained in the fluid being sucked back into the passages 5 so that the material is aspirated out of the cavity by the suction device 11.

What is claimed is:

1. Apparatus for preparing a medullary cavity during endoprosthetic surgery of long bones, the apparatus comprising:

a hollow shaft having a longitudinal axis and having first and second ends, the hollow shaft defining a wall surrounding a central bore;

an offset lug on the first end of the hollow shaft, the lug extending obliquely with respect to the axis and being adapted to receive a handle;

a first opening adjacent the lug and communicating with the bore and a second opening through the second end of the hollow shaft, the first and second openings cooperating to facilitate irrigating and aspirating the cavity as the cavity is prepared by the shaft;

spaced peripheral teeth extending radially outwardly from the wall of the shaft, the teeth having cutting edges for removing material from the wall of the medullary cavity; and passages through the wall of the hollow shaft, the passages being adjacent to peripheral teeth and communicating with the bore in the shaft for receipt of material removed by the teeth, whereby the material is entrained in fluid dispensed through the second opening and aspirated via the passages for removal from the cavity.

2. The apparatus of claim 1, wherein the teeth have cutting edges which face in the direction of the second end.

3. The apparatus of claim 1, wherein the teeth are staggered along the longitudinal axis and the hollow shaft tapers from the first end to the second end.

4. The apparatus of claim 1, wherein the cutting edges of the teeth face radially and extend longitudinally so that the apparatus functions as an awl.

5. The apparatus of claim 1, wherein a central tube extends in the bore and opens at the second opening for delivering irrigation fluid to the cavity, which irrigation fluid is sucked by a suction device connected to the bore through the passages in the wall adjacent the teeth so as to remove material from the cavity.

\* \* \* \* \*